US00PP32546P2

(12) United States Plant Patent
Schroll

(10) Patent No.: US PP32,546 P2
(45) Date of Patent: Dec. 1, 2020

(54) ***HYDRANGEA* PLANT NAMED 'SCHROLL130-12-01A'**

(50) Latin Name: *Hydrangea macrophylla*
Varietal Denomination: SCHROLL130-12-01a

(71) Applicant: Soren Schroll, Odense SV (DK)

(72) Inventor: Soren Schroll, Odense SV (DK)

(73) Assignee: SCHROLL MANAGEMENT ApS, Odense SV (DK)

( * ) Notice: Subject to any disclaimer, the term of this patent is extended or adjusted under 35 U.S.C. 154(b) by 0 days.

(21) Appl. No.: 16/873,043

(22) Filed: Jan. 21, 2020

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Hydrangea* plant named 'SCHROLL130-12-01a', characterized by its upright and mounded plant habit; vigorous growth habit; freely branching habit and moderately strong stems; dark green-colored leaves; large mophead-type inflorescences with white-colored sterile flowers that are initially pale yellow green in color; long flowering period; and good postproduction quality and longevity.

2 Drawing Sheets

Figure 1:
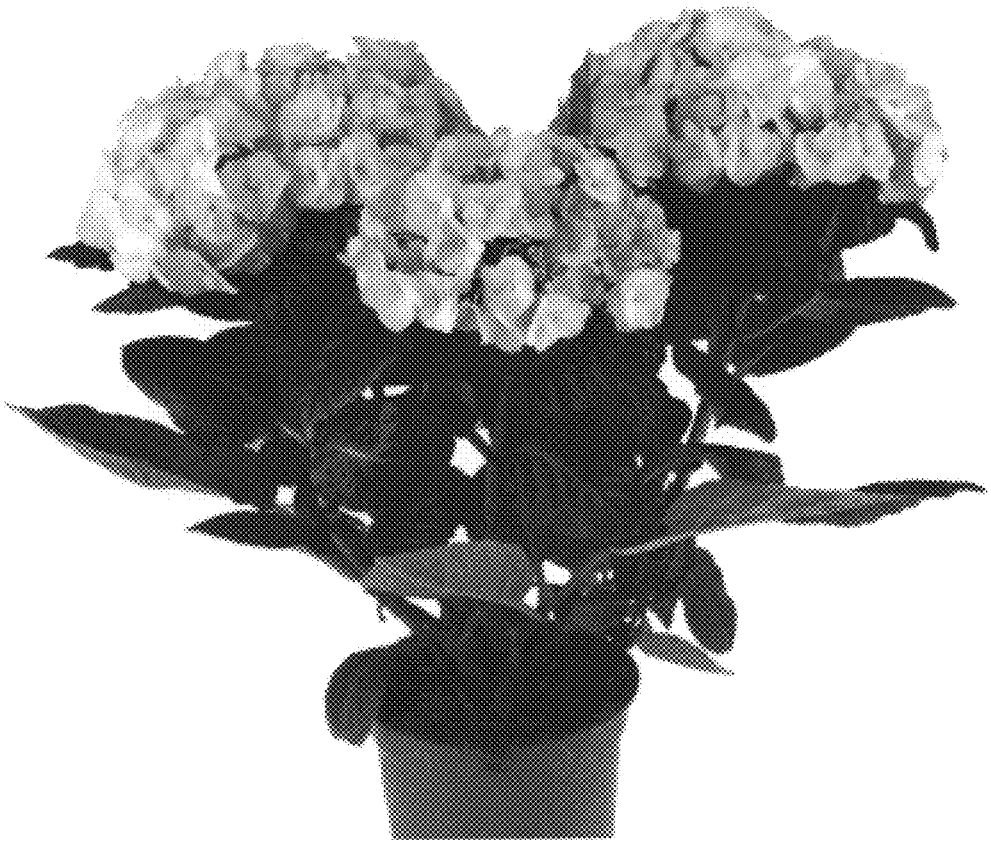

Botanical designation: *Hydrangea macrophylla.*
Cultivar denomination: 'SCHROLL130-12-01a'.

BACKGROUND OF THE INVENTION

The present invention relates to a new and distinct cultivar of *Hydrangea* plant, botanically known as *Hydrangea macrophylla* and hereinafter referred to by the name 'SCHROLL130-12-01a'.

The new *Hydrangea* plant is a product of a planned breeding program conducted by the Inventor in Aarslev, Denmark. The objective of the breeding program was to develop new container-type *Hydrangea* plants with strong stems, early flowering response and attractive leaf and flower coloration.

The new *Hydrangea* plant originated from a cross-pollination during the spring of 2012 of a proprietary selection of *Hydrangea macrophylla* identified as code number 11-00, not patented, as the female, or seed, parent with a proprietary selection of *Hydrangea macrophylla* identified as code number 27-00, not patented, as the male, or pollen, parent. The new *Hydrangea* plant was discovered and selected by the Inventor in February, 2014 as a flowering plant from within the progeny of the stated cross-pollination in a controlled greenhouse environment in Aarslev, Denmark.

Asexual reproduction of the new cultivar by softwood cuttings in Aarslev, Denmark since the spring of 2015 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SCHROLL130-12-01a'. These characteristics in combination distinguish 'SCHROLL130-12-01a' as a new and distinct *Hydrangea* plant:

1. Upright and mounded plant habit.
2. Vigorous growth habit.
3. Freely branching habit and moderately strong stems.
4. Dark green-colored leaves.
5. Large mophead-type inflorescences with white-colored sterile flowers that are initially pale yellow green in color.
6. Long flowering period.
7. Good postproduction quality and longevity.

Plants of the new *Hydrangea* differ primarily from plants of the female selection parent in the following characteristics:

1. Plants of the new *Hydrangea* have larger and denser inflorescences than plants of the female parent selection.
2. Plants of the new *Hydrangea* are more freely flowering than plants of the female parent selection.
3. Inflorescences of plants of the new *Hydrangea* are mophead types whereas inflorescences of plants of the female parent selection are lacecap types.
4. Plants of the new *Hydrangea* and the female parent selection differ in sterile flower color as sterile flowers of plants of the new *Hydrangea* are white in color whereas sterile flowers of plants of the female parent selection are dark pink in color.
5. Inflorescences of plants of the new *Hydrangea* are longer lasting than inflorescences of plants of the female parent selection.

Plants of the new *Hydrangea* differ primarily from plants of the male selection parent in the following characteristics:

1. Plants of the new *Hydrangea* are more compact than and not as vigorous as plants of the male parent selection.
2. Plants of the new *Hydrangea* are more freely flowering than plants of the male parent selection.
3. Plants of the new *Hydrangea* and the male parent selection differ in sterile flower color as sterile flowers of plants of the new *Hydrangea* are white in color whereas sterile flowers of plants of the male parent selection are pink in color.
4. Sterile flowers of plants of the new *Hydrangea* are single types whereas sterile flowers of plants of the male parent selection are double types.
5. Inflorescences of plants of the new *Hydrangea* are longer lasting than inflorescences of plants of the male parent selection.

Plants of the new *Hydrangea* can be compared to plants of *Hydrangea macrophylla* 'H213901', disclosed in U.S. Plant Pat. No. 26,221. Plants of the new *Hydrangea* differ primarily from plants of 'H213901' in the following characteristics:

1. Plants of the new *Hydrangea* are more compact than and not as vigorous as plants of 'H213901'.
2. Plants of the new *Hydrangea* are more freely branching than plants of 'H213901'.
3. Inflorescences of plants of the new *Hydrangea* are larger and flatter than inflorescences of plants of 'H213901'.
4. Sepals of sterile flowers of the new *Hydrangea* are not as undulate as sepals of sterile flowers of 'H213901'.
5. Plants of the new *Hydrangea* and 'H213901' differ in sterile flower color as sterile flowers of plants of the new *Hydrangea* are white in color whereas sterile flowers of plants of 'H213901' are dark red purple in color.

Plants of the new *Hydrangea* can be compared to plants of *Hydrangea macrophylla* 'H213906', disclosed in U.S. Plant Pat. No. 26,509. Plants of the new *Hydrangea* differ primarily from plants of 'H213906' in the following characteristics:

1. Plants of the new *Hydrangea* have glossier leaves than plants of 'H213906'.
2. Plants of the new *Hydrangea* force slower than plants of 'H213906'.
3. Plants of the new *Hydrangea* are not as freely flowering as plants of 'H213906'.
4. Plants of the new *Hydrangea* and 'H213906' differ in sterile flower color as sterile flowers of plants of the new *Hydrangea* are white in color whereas sterile flowers of plants of 'H213906' are dark pink in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1 of 2) comprises a side perspective view of a typical flowering plant of 'SCHROLL130-12-01a' grown in a container.

Figure 2:
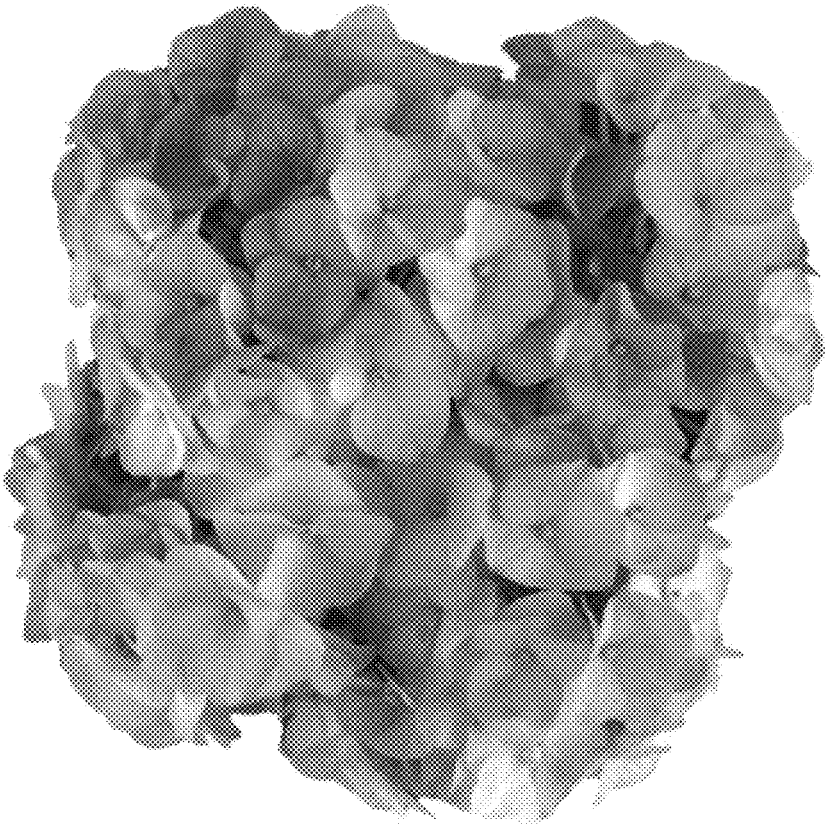

The photograph on the second sheet (FIG. 2 of 2) is a close-up view of a typical inflorescence of 'SCHROLL130-12-01a'.

DETAILED BOTANICAL DESCRIPTION

Plants used in the aforementioned photographs and in the following description were grown during the spring in 13-cm containers in a glass-covered greenhouse in Aarslev, Denmark and under cultural practices typical of commercial *Hydrangea* production. Plants of the new *Hydrangea* were pinched two times and were one year old when the photographs and description were taken. During the production of the plants, day temperatures ranged from 15° C. to 25° C. and night temperatures ranged from 10° C. to 20° C. and light levels ranged from 40 to 50 klux. Plants are typically not "blued", that is, treated with aluminum sulfate to change the color of the inflorescences. In the following description, color references are made to The Royal Horticultural Society Colour Chart, 2007 Edition, except where general terms of ordinary dictionary significance are used.

Botanical description: *Hydrangea macrophylla* 'SCHROLL130-12-01a'.

Parentage:

*Female, or seed, parent*.—Proprietary selection of *Hydrangea macrophylla* identified as code number 11-00, not patented.

*Male, or pollen, parent*.—Proprietary selection of *Hydrangea macrophylla* identified as code number 27-00, not patented.

Propagation:

*Type cutting*.—By softwood cuttings.

*Time to initiate roots, summer*.—About ten days at temperatures about 19° C. to 22° C.

*Time to initiate roots, winter*.—About two weeks at temperatures about 18° C. to 20° C.

*Time to produce a rooted young plant, summer*.—About four weeks at temperatures about 18° C. to 20° C.

*Time to produce a rooted young plant, winter*.—About five weeks at temperatures about 18° C. to 20° C.

*Root description*.—Medium in thickness, fibrous; white, close to N155D, in color.

*Rooting habit*.—Sparse; not freely branching.

Plant description:

*Plant and growth habit*.—Perennial subshrub; upright and mounded plant habit; broadly inverted triangle; freely branching habit with about eight to ten lateral branches developing per plant; moderately strong lateral branches; vigorous growth habit.

*Plant height*.—About 38 cm.

*Plant diameter or area of spread*.—About 60 cm.

*Lateral branches*.—Length: About 25 cm to 30 cm. Diameter: About 4 mm to 6 mm. Internode length: About 7 cm to 9 cm. Strength: Moderately strong, sturdy. Texture: Smooth, glabrous. Color, developing and developed: Close to 144A to 144B; at the nodes close to 79A. Color, lenticels: Close to N199B.

Leaf description:

*Arrangement*.—Opposite, decussate; simple.

*Length*.—About 8 cm to 10 cm.

*Width*.—About 8 cm to 10 cm.

*Shape*.—Ovate.

*Apex*.—Cuspidate.

*Base*.—Obtuse.

*Margin*.—Serrate.

*Texture, upper surface*.—Smooth to rugose, glabrous.

*Texture, lower surface*.—Rugose, glabrous.

*Venation pattern*.—Pinnate, reticulate.

*Color*.—Developing leaves, upper surface: Close to 137A. Developing leaves, lower surface: Close to 137C. Fully expanded leaves, upper surface: Close to 137A; venation, close to 145C to 145D. Fully expanded leaves, lower surface: Close to 137D; venation, close to 145C to 145D.

*Petioles*.—Length: About 3 cm. Diameter: About 3 mm to 5 mm. Strength: Strong. Texture, upper and lower surfaces: Smooth, glabrous. Color, upper surface: Close to 144A. Color, lower surface: Close to 144B.

Inflorescence & flower description:

*Flower type and habit*.—Showy single sterile and inconspicuous single fertile flowers arranged on terminal mophead-type panicles; panicles flattened globular in overall shape; fertile flowers face upright to outwardly and sterile flowers face mostly upright to outwardly depending on their position on the inflorescence; medium flowering habit, plants begin flowering about ten to twelve weeks after forcing period.

*Natural flowering season*.—Long flowering period, continuous flowering from the later summer (July/August) until frost in Northern Europe.

*Flower longevity, fertile flowers*.—Flowers last about three to five weeks on the plant; fertile flowers persistent.

*Flower longevity, sterile flowers*.—Flowers last about four months on the plant; sterile flowers persistent.

*Quantity of flowers*.—Freely flowering habit with about 30 fertile flowers and about 150 sterile flowers per panicle.

*Fragrance*.—None detected.

*Panicle height*.—About 8 cm.

*Panicle diameter*.—About 18 cm to 20 cm.

*Flower diameter, fertile flowers*.—About 3 mm to 4 mm.

*Flower depth* (*height*), *fertile flowers*.—About 2 mm to 3 mm.

*Flower diameter, sterile flowers*.—About 4 cm.

*Flower depth* (*height*), *sterile flowers*.—About 1 cm.

*Flower shape, fertile flowers*.—Spherical.

*Flower shape, sterile flowers*.—Rounded, flat.

*Flower buds, fertile flowers*.—Length: About 2 mm to 3 mm. Diameter: About 2 mm to 3 mm. Shape: Spherical. Color: Close to 155C.

*Flower buds, sterile flowers*.—Length: About 3 mm. Diameter: About 3 mm. Shape: Spherical. Color: Close to 1C.

*Petals, fertile flowers*.—Quantity and arrangement: Four to five in a single whorl. Length: About 4 mm to 5 mm. Width: About 2 mm. Shape: Obovate to ovate. Apex: Obtuse. Base: Rounded. Margin: Entire. Texture, upper and lower surfaces: Smooth, glabrous. Color: When opening, upper and lower surfaces: Close to NN155A. Fully opened, upper and lower surfaces: Close to NN155C; color does not change with development.

*Petals, sterile flowers*.—Quantity and arrangement: Four to six in a single whorl. Length: About 2.2 mm. Width: About 2.2 mm. Shape: Ovate. Apex: Acute, curved upright. Base: Truncate. Margin: Entire. Texture, upper and lower surfaces: Smooth, glabrous. Color: When opening, upper and lower surfaces: Close to NN155D. Fully opened, upper and lower surfaces: Close to NN155D; color does not change with development.

*Sepals, fertile flowers*.—Quantity and arrangement: About five in a single whorl. Length: About 2 mm to 3 mm. Width: About 1 mm to 2 mm. Shape: Deltoid. Apex: Acute. Base: Rounded. Margin: Entire. Texture, upper and lower surfaces: Smooth, glabrous. Color: When opening, upper and lower surfaces: Close to 150B. Fully opened, upper and lower surfaces: Close to 150B; color does not change with development.

*Sepals, sterile flowers*.—Quantity and arrangement: Four to six in a single whorl. Length: About 2.5 cm. Width: About 3 cm. Shape: Deltoid to oval. Apex: Retuse. Base: Broadly cuneate. Margin: Entire. Texture, upper surface: Smooth to slightly rippled, glabrous. Texture, lower surface: Smooth, glabrous. Color: When opening, upper and lower surfaces: Initially, pale yellow green, close to 154C; subsequently, close to 1D. Fully opened, upper surface: Close to 155C; color becoming closer to 145C with development. Fully opened, lower surface: Close to 155D; color becoming closer to 145D with development.

*Pedicels, fertile flowers*.—Length: About 1 cm to 1.5 cm. Diameter: About 1 mm. Strength: Strong. Aspect: Mostly upright. Texture: Smooth, glabrous. Color: Close to NN155D.

*Pedicels, sterile flowers*.—Length: About 3.5 cm. Diameter: About 1.5 mm. Strength: Moderately strong. Aspect: Less than 90° from vertical. Texture: Pubescent. Color: Close to 155D.

*Reproductive organs, fertile flowers*.—Stamens: Quantity per flower: About eight. Filament length: About 1 mm to 2 mm. Filament color: Close to NN155D. Anther length: About 1 mm. Anther shape: Ovate. Anther color: Close to 155D. Pollen amount: Abundant. Pollen color: Close to NN155D. Pistils: Pistil quantity per flower: About three. Pistil length: Less than 1 mm. Stigma shape: Oblong. Stigma color: Close to NN155D. Style length: Less than 1 mm. Style color: Close to NN155D. Ovary color: Close to NN155D.

*Reproductive organs, sterile flowers*.—Stamens: Quantity per flower: About six to eight. Filament length: About 3 mm to 5 mm. Filament color: Close to 155D. Anther length: About 1 mm to 2 mm. Anther shape: Ovate. Anther color: Close to 155D. Pollen amount: Scarce. Pollen color: Close to 155D. Pistils: Pistil quantity per flower: About three. Pistil length: About 1 mm to 2 mm. Stigma shape: Oblong. Stigma color: Close to 155D. Style length: Less than 1 mm Style color: Close to 155D. Ovary color: Close to 155D.

*Seeds*.—To date, seed development has not been observed on plants of the new *Hydrangea*.

Pathogen & pest resistance: To date, plants of the new *Hydrangea* have not been observed to be resistant to pathogens and pests common to *Hydrangea* plants.

Temperature tolerance: Plants of the new *Hydrangea* have been shown to be tolerant to temperatures ranging from about 1° C. to 38° C.

It is claimed:

1. A new and distinct *Hydrangea* plant named 'SCHROLL130-12-01a' as illustrated and described.

* * * * *